United States Patent [19]
Weber et al.

[11] Patent Number: 5,748,479
[45] Date of Patent: May 5, 1998

[54] METHOD OF NEUTRALIZING HOT INCLUSIONS PRESENT IN A WEB OF MINERAL WOOL AND APPARATUS FOR CARRYING OUT THE METHOD

[75] Inventors: Gerd Weber, Neuburg; Willi Biebel, Rennertshofen, both of Germany

[73] Assignee: Deutsche Rockwool Mineralwall-GmbH, Gladbeck, Germany

[21] Appl. No.: 607,891

[22] Filed: Feb. 27, 1996

[30] Foreign Application Priority Data

Mar. 4, 1995 [DE] Germany .................. 195 07 643.5

[51] Int. Cl.[6] .................. C03G 13/06; C03B 37/10
[52] U.S. Cl. .................. 364/470.01; 364/468.01; 364/468.19; 364/469.01
[58] Field of Search .................. 364/470.01, 552, 364/555–559, 468.01, 468.19, 469.01; 501/36

[56] References Cited

U.S. PATENT DOCUMENTS

| | | | |
|---|---|---|---|
| 4,106,163 | 8/1978 | Desverchere | 19/296 |
| 4,210,432 | 7/1980 | Brelen et al. | 65/377 |
| 4,337,074 | 6/1982 | Muschelknautz et al. | 65/466 |
| 4,688,301 | 8/1987 | Thorbjornsson et al. | 19/296 |
| 4,988,875 | 1/1991 | Ortiz et al. | 250/330 |
| 5,270,787 | 12/1993 | Shofner et al. | 73/160 |
| 5,383,135 | 1/1995 | Shofner et al. | 364/552 |
| 5,487,655 | 1/1996 | Frey et al. | 425/72.2 |

FOREIGN PATENT DOCUMENTS

| | | |
|---|---|---|
| 0 606 626 A1 | 7/1994 | European Pat. Off. . |
| 3928279 A1 | 2/1991 | Germany . |

OTHER PUBLICATIONS

Database WPI, Week 8405, Derwent Publications Ltd., AN 84–028106; and SU, A, 1 006 397 (Teploproekt Res Des Inst), 23 Mar. 1983.

Database WPI, Week 9306, Derwent Publications Ltd., AN 93–051753; and Su, A, 1 719 328 (Thermal Insulation Materials Cons Techn), 15 Mar. 1992.

Patent Abstracts of Japan; vol. 011, No. 383 (P–646), 15 Dec. 1987 and JP, A, 63 150146 (Japan Vilene Co., Ltd.).

Journal of Applied Physics, vol. 70, No. 10, Pt. 1, 15 Nov. 1991, pp. 5221–5223, Eickmeier et al. "Inspection of Transparent Polymers by Photothermal Detection of Ultraviolet-Laser Generated Thermal Waves".

Primary Examiner—Emanuel T. Voeltz
Assistant Examiner—Hien Vo
Attorney, Agent, or Firm—Liddell, Sapp, Zivley, Hill & LaBoon, L.L.P.

[57] ABSTRACT

The production of mineral wool takes place by melting stones, with the melt being supplied to a defibration unit. During this production process hot inclusions which are detrimental to further processing and to the final product may get into the mineral wool. To provide a method suitable for producing a homogeneous web of mineral wool free from influences by hot inclusions, the position of the hot inclusions are localized by a sensor. Position measuring data is used for controlling the nozzle system which acts upon the hot inclusions.

20 Claims, 2 Drawing Sheets

METHOD OF NEUTRALIZING HOT INCLUSIONS PRESENT IN A WEB OF MINERAL WOOL AND APPARATUS FOR CARRYING OUT THE METHOD

FIELD OF THE INVENTION

This invention relates to a method of neutralizing hot inclusions present in a web of mineral wool.

BACKGROUND OF THE INVENTION

The production of mineral wool takes place by melting stones like diabase, basalt, lime and the like in suitable melting units like cupola melting furnaces or tanks to a silicious melt which is supplied to a defibration unit such as a cascade spinner. Said defibration unit defibrates the melt into fine mineral fibers which then form flocks of mineral wool which in turn are fed to a collecting chamber by means of an air stream under simultaneous addition of a suitable bonding agent. Within the collecting chamber, mostly on the bottom thereof, there is a perforated endless continuously driven collecting chamber belt by which air that has been introduced is evacuated to a suction chamber. Thereby the fine wool flocks are deposited onto the collecting chamber belt.

The basis weight of the thus produced primary web is determined on one hand by the material flow from the defibration unit and on the other hand by the speed of the collecting chamber belt at which the primary web is delivered from the collecting chamber. Depending on the selection of the speed of the collecting chamber belt, primary webs of several kg basis weight can be produced which may be supplied subsequently or directly to a hardening furnace wherein they are hardened under pressure so that the desired bulk density and thickness of the product can be set.

Another possibility resides in producing a primary web of a low basis weight and to treat the same by individual layers transversely of the delivery direction in pendulum fashion so that the desired basis weight is obtained. The thus produced secondary web is then supplied to a hardening furnace wherein the hardening furnace belts transmit a compressive strain to the secondary web in order to set the desired bulk density and thickness.

As mentioned above, natural stones like basalts, diabase as well as sedimentary rocks and silicious slag are used as the raw materials for the production of a silicious melt. These natural raw materials may contain high-melting impurities which cannot be melted during the melting process and are discharged from the melting unit as hot solids. If the raw materials are melted by applying the cupola furnace method, the energy required therefor will be provided through coke. With this melting method, live coke pieces may leave the cupola furnace with the melt. When the said particles, i.e. the hot solids and the live coke pieces, reach the collecting chamber they do not cool down to the same extent as the mineral wool fibers so that they may get into the mineral wool and finally into the finished product in their hot state. Once the hot particles or inclusions are embedded in a web of mineral wool, they cool down only slowly due to the fact that the surrounding mineral wool represents a heat insulation material which makes it more difficult to carry away the heat. In addition, by the hot inclusions the organic bonding agent, mostly phenolic resin, used in the production of insulation materials is decomposed in an exothermal process during which temperatures may be generated exceeding the sintering temperature of the surrounding fiber mass so that the insulation material in the adjacencies of the hot inclusions may become fully destroyed, resulting in that the final product is frequently damaged to an extent not allowing its further use. Since this process of destruction may expand to several days, difficulties concerning safety arise even during the further processing and up to storage.

SUMMARY OF THE INVENTION

The invention is based on the object of providing a method allowing the production of a homogeneous web of mineral wool free from any influence by hot inclusions.

According to the invention, this object is solved in that the position of the hot inclusions is localized by means of a sensor and that the position measuring data obtained in the sensor are used for controlling a nozzle system acting upon said hot inclusions.

An advantageous embodiment of the method is characterized in that the nozzle system is controlled so that big inclusions are removed from the web of mineral wool and small inclusions which are not detrimental to the material are cooled.

Another advantage resides in the pressure of the nozzle system being regulated in response to the size and thermal capacity of the detected inclusion.

Furthermore, it has shown to be an advantage if an infrared or thermal camera are used as a sensor being associated with a computer used to generate the position measuring data for controlling the nozzle system.

In a further embodiment of the method according to the invention, a line camera is used as the sensor which successively scans the entire width of the continuously conveyed web of mineral wool in a line by line fashion so that a thermal image of the web of mineral wool is produced and the corresponding nozzle system control data are generated by a computer.

The method turned out to be particularly effective if the nozzle system is operated at a pressure of more than $180 \times 10^5$ Pa up to approx $1000 \times 10^5$ Pa.

The high pressure nozzles are preferably charged with air or water. The special advantage of the method according to the invention is to be seen in the air or water nozzles being effective only within a limited space and only for a short time so that the primary web treated by the nozzle system is maintained of its basic substance and the process does not take any influence on the ultimate completion of the final product. This particularly applies if a thin primary web is produced first which in a downstream pendulum unit is folded open transversely of the conveying direction so that a secondary web of much greater thickness is produced which does no longer present any inclusions and therefore can be advanced in a homogeneous state to a hardening furnace known per se for curing the bonding agent.

The invention further relates to an apparatus for carrying out the method, said apparatus comprising a collecting chamber wherein a web of mineral wool is formed on a continuously driven conveying means and is discharged from the collecting chamber.

The apparatus according to the invention is characterized in that a sensor is provided which is deviced and arranged so that hot inclusions in the web of mineral wool are localized at the smallest possible interval after delivery of the web of mineral wool from the collecting chamber and that a nozzle system is provided at a distance from the sensor which corresponding to the position measuring data generated within the sensor can be operated so that a nozzle jet acts upon every one of the hot inclusions.

DETAILED DESCRIPTION OF THE INVENTION

Figure 1:
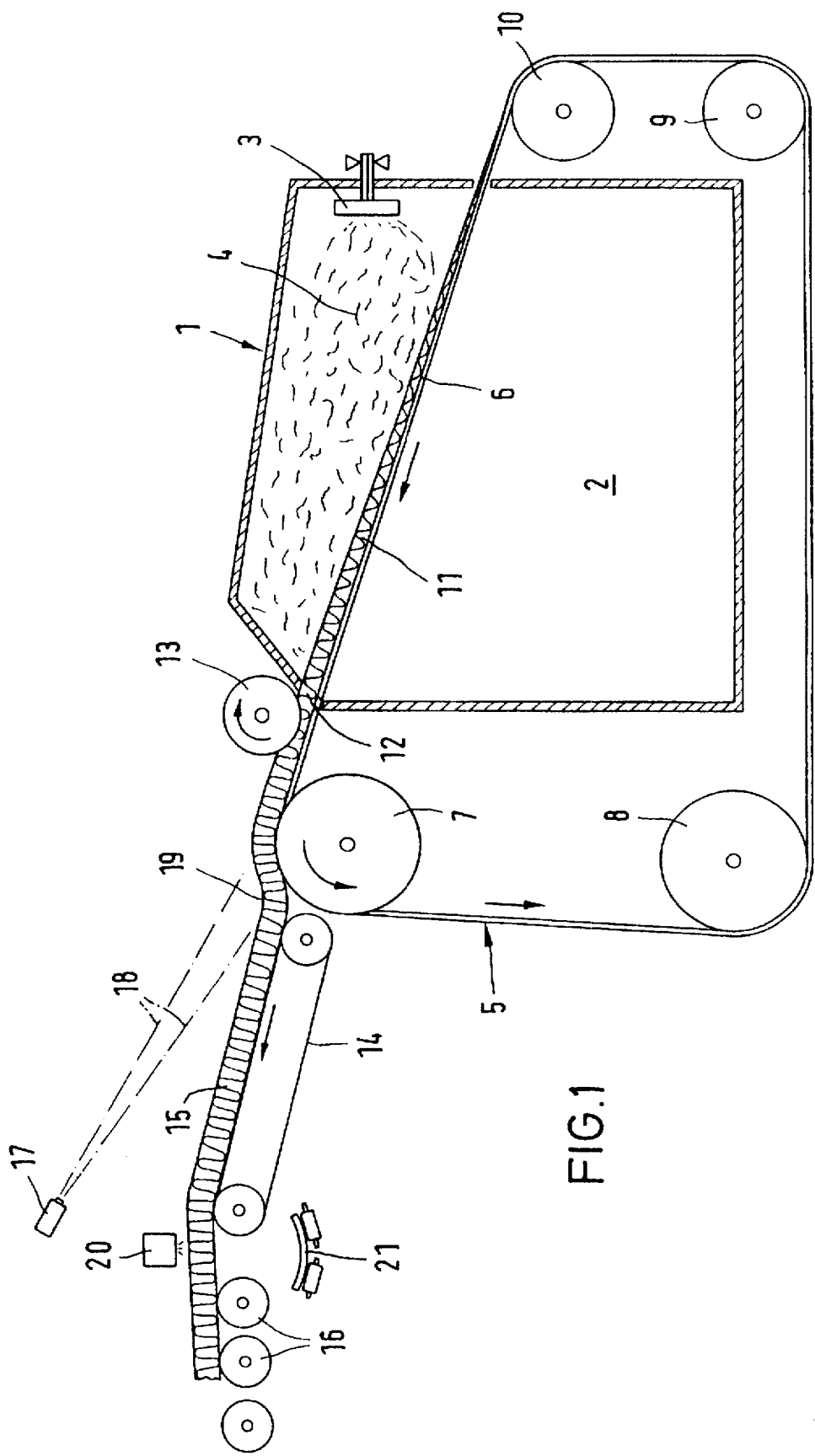
FIG. 1 is a schematical side view, partly in vertical section, of a collecting chamber with an apparatus according to the invention annexed to it.

In FIG. 1 there is schematically represented a collecting chamber 1 with a suction chamber 2 and defibration unit 3, which is charged in the conventional manner with a melt so that mineral fibers 4 are ejected which are sprayed with a bonding agent and accumulate to a primary web or web of mineral wool 11 on the upper sloping trunk 6 of an air permeable endless conveyor belt 5. In this embodiment, the endless conveyor belt 5 is passed around deflection pulleys 7, 8, 9 and 10 and is continuously driven in the direction of the arrow. The primary web 11 leaves the collecting chamber at a delivery slot 12, on which location a seal roller 13 is arranged above the web of mineral wool, said seal roller on one hand serving to seal the delivery slot 12 and on the other hand for the compacting of the web of mineral wool 11 to a continuously advanced web of mineral wool. After passing from the endless conveyor belt 5 within the zone of the deflection pulley 7 the web of mineral wool 15 gets onto an endless conveyor belt 14 and from there, leaving a transversely extending slot of approx 3 cm width, to a further line conveyor 16, for example in the form of a driven roller table.

As further shown by the schematical representation of FIG. 1, a sensor 17 is provided which is deviced and arranged so that hot inclusions in the web of mineral wool are detected or localized at the smallest possible interval after delivery 12 of the web of mineral wool 11, 15 from the collecting chamber 1. In this embodiment, the direction of view of the sensor 17, which is represented by chain lines 18, meets with a portion 19 of the web of mineral wool 15, namely over the total width of the web of mineral wool and therefore seen vertically to the focal plane of FIG. 1. At a distance from the sensor a nozzle system 20 is provided which is operable corresponding to the position measuring data generated within the sensor 17 so that a nozzle jet acts upon every hot inclusion which is present in the web of mineral wool 15.

Figure 2:
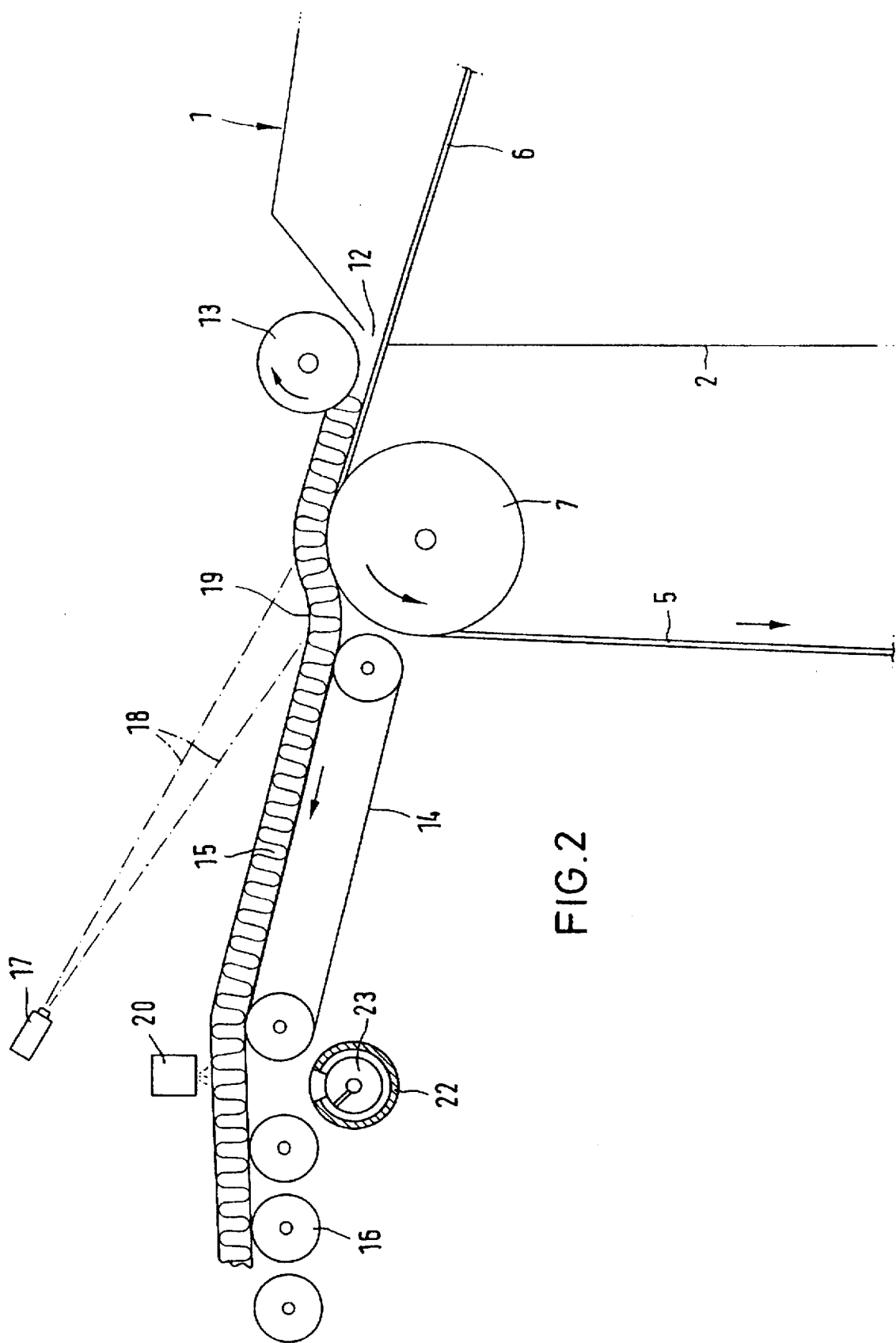
FIG. 2 is a detail from FIG. 1 on an enlarged scale.

The nozzle system is constructed to be operated so that hot inclusions of big size are removed or blown out from the web of mineral wool 15 by a strong nozzle jet. The big inclusions pass through the slot between the two line conveyors 14 and 16 onto delivery means 21 which, according to FIG. 2, can be for example in the form of a cooled sheet metal channel or, according to FIG. 2, in the form of a driven worm 23 within a worm trough. However, the nozzle system 20 is also formed so that small inclusions which are harmless to the material are merely cooled by a nozzle jet.

Advantageously, the sensor 17 is comprised of an infrared or thermal camera and a computer wherein the position measuring data are generated with regard to the hot inclusions for controlling the nozzle system 20. Advantageously, the sensor 17 may comprise a line camera which is deviced and arranged so that it successively scans line by line the total width of the continuously conveyed web of mineral wool, that it produces a thermal image of the web of mineral wool and generates the corresponding control data and outputs said data to the nozzle system 20.

According to an advantageous embodiment of the apparatus according to the invention, the nozzle system 20 comprises a plurality of individual nozzles which are arranged above the web of mineral wool so as to be spaced apart and distributed transversely of the conveying direction of the web of mineral wool 15 over the entire width thereof, each individual nozzle being selectable by a computer. Expediently, the nozzle system is equipped with high pressure nozzles suitable for pressures between 180 up to $1000 \times 10^5$ Pa. The high pressure nozzles can be selectively constructed as air or water jet nozzles. If water jet nozzles are used, the so-called fan jet nozzles will be particularly suited. A special construction is obtained by the nozzle system 20 comprising a nozzle bar extending transversely of the conveying direction of the web of mineral wool 15 and having mounted thereon the individual nozzles with the respective control means. Another special aspect is obtained by the thermal image within the line camera being divided in sectors which are each associated with a downstream water or air nozzle in the nozzle system. Depending on the degree of the screening density, a plurality of nozzles will have to be arranged transversely of the conveying direction.

The essential function of the above described apparatus according to the invention is as follows. When a hot inclusion in the web of mineral wool is detected or localized by the sensor, for example the thermal camera, the downstream computer determines its position and allocates the same to a downstream nozzle in the nozzle system. Further, the time is determined in response to the conveying speed, i.e. the time by which the hot inclusion reaches the corresponding nozzle. Reaching said nozzle, the inclusion is so to speak catapulted from the web of mineral wool and drops onto the delivery means 21 respectively 22, 23 which is arranged below the web of mineral wool 15 to discharge the hot particles from the apparatus and transfer these particles to a location where they can be cooled or allowed to cool. It will be understood that the respective nozzle is operated for a short time only. Materials are used for the high pressure nozzles having properties which prevent after-dripping in the case where water jet nozzles are applied.

To generalize, the following aspects may be added. The cooling and transporting function of the nozzle jets of the nozzle system essentially depend from the mass of the corresponding gas or liquid stream as well as from the velocity of the nozzle jet. The regulation of the nozzle system therefore takes place according to the respective locally prevailing conditions. If, in the one extreme case, the matter is especially about cooling merely hot inclusion of small size, a short water jet without considerable pressure will be sufficient which means in the borderline case that cooling is effected merely under gravity force of the water jet. The faster the cooling or delivery of hot inclusions is to take place and the bigger the inclusions are, the higher the gas or liquid pressure of the nozzle system must be regulated, but in the majority of cases a pressure of $5 \times 10^5$ Pa will be sufficient already, particularly for cooling.

An alternative to the above described line camera is obtained by arranging the sensor stationary, however, swivelling to and fro very rapidly so that during its swivelling motion the sensor will scan the continuously conveyed web of mineral wool and localize the existing hot inclusions so to speak line by line. A constructional alternative exists also in respect of the nozzle system. According to this alternative, only a single nozzle system is arranged to reciprocate on a carriage extending across the web of mineral wool. This construction results in a considerable simplification, especially concerning the control of the nozzle system, so that it should be selected preferably in the case where the hot inclusions which are harmful in the final product do relatively rarely occur.

We claim:

1. A method of neutralizing hot inclusions in a web of mineral wool which comprises:
   (a) applying hot particles of mineral fibers onto mineral wool as it passes on a conveyer and discharging the resulting web from a collecting chamber;
   (b) localizing hot inclusions in the web of mineral wool after delivery of the web from the collecting chamber by means of a sensor;
   (c) directing a nozzle jet system on the mineral wool web at positions corresponding to those generated by the sensor means; and
   (d) removing large inclusions from the mineral web by means of the nozzle jet system.

2. The method according to claim 1, characterized by the nozzle system being controlled so that big inclusions are removed from the web of mineral wool and small inclusions which are harmless to the material are cooled.

3. The method according to claim 2, characterized in that an infrared of thermal camera are used as the sensor being associated with a computer by means of which the position measuring data are generated for controlling the nozzle system.

4. The method according to claim 2, characterized in that the pressure of the nozzle system is regulated in response to the size and thermal capacity of the detected inclusion.

5. The method according to claim 1, characterized in that the pressure of the nozzle system is regulated in response to the size and thermal capacity of the detected inclusion.

6. The method according to claim 1, characterized in that a line camera is used as the sensor which successively scans in a line by line fashion the entire width of the continuously conveyed web of mineral wool so that a thermal image of the web of mineral wool is produced and the corresponding control data for the nozzle system (20) are generated by a computer.

7. A method according to claim 1, characterized in that the nozzle system is operated at a pressure of more than 180× $10^5$ Pa up to approx $1000 \times 10^5$ Pa.

8. An apparatus for neutralizing hot inclusions in a web of mineral wool which comprises:
   (a) a conveying means for transferring the mineral wool;
   (b) a means for ejecting mineral fibers onto the mineral wool;
   (c) a collecting chamber for receiving the mineral wool web;
   (d) a sensor means for localizing hot inclusions in the mineral wool web and generating data therein regarding the position of said inclusions; and
   (e) a nozzle jet system for removing the inclusions.

9. The apparatus according to claim 8, characterized in that the nozzle system can be operated so that big inclusions are removed or blown out from the web of mineral wool and small inclusions which are harmless to the material are cooled.

10. The apparatus according to claim 8, characterized in that the sensor is comprised of an infrared or thermal camera and a computer wherein the position measuring data for controlling the nozzle system are generated.

11. The apparatus according to claim 8, characterized in that the sensor comprises a line camera which is devised and arranged so as to successively scan the entire width of the continuously conveyed web of mineral wool in a line by line fashion, to produce a thermal image of the web of mineral wool and to generate the control data through a computer and to output these data to the nozzle system.

12. The apparatus according to claim 11, characterized by the thermal image within a line camera being divided in sectors and each sector having allocated a downstream water or air nozzle.

13. The apparatus according to claim 8, characterized in that the nozzle system comprises a plurality of individual nozzles which are arranged above the web of mineral wool transversely of the conveying direction so as to be spaced apart and distributed over the entire width thereof and that each individual nozzle can be selected by the computer.

14. The apparatus according to claim 13, characterized in that below the nozzle system in the conveying means (14,16) for the web of mineral wool a transversely extending slot is provided through which the blown out hot inclusions leave and get onto a cross conveyor.

15. The apparatus according to claim 8, characterized by the nozzle system being equipped with high pressure nozzles for pressures between 180 to $1000 \times 10^5$ Pa.

16. The apparatus according to claim 15, characterized by the high pressure nozzles being selectively formed as air or water jet nozzles.

17. The apparatus according to claim 16, characterized by the water jet nozzles being formed as fan jet nozzles.

18. The apparatus according to claim 8, characterized in that below the nozzle system in the conveying means for the web of mineral wool a transversely extending slot is provided through which the blown out hot inclusions leave and get onto a cross conveyor.

19. The apparatus according to claim 18, characterized in that the cross conveyor is comprised of a cooled sheet metal channel and a worm conveyor.

20. The apparatus according to claim 8, characterized in that the nozzle system comprises a transversely extending slot is provided through which the blown out hot inclusions leave and get onto a cross conveyor.

* * * * *